United States Patent [19]

Paget

[11] 4,382,028

[45] May 3, 1983

[54] SEPARATION OF PLASMA PROTEINS FROM CELL CULTURE SYSTEMS

[75] Inventor: G. Edward Paget, Chesterfield, Mo.

[73] Assignee: Monsanto Company, St. Louis, Mo.

[21] Appl. No.: 399,604

[22] Filed: Jul. 19, 1982

[51] Int. Cl.$^3$ .............................................. C07G 7/00
[52] U.S. Cl. ................................ 260/112 B; 260/122; 424/101; 424/177
[58] Field of Search ............................ 260/112 B, 122; 424/101

[56] References Cited

U.S. PATENT DOCUMENTS

| | | | |
|---|---|---|---|
| 3,554,985 | 1/1971 | Fields et al. ...................... | 260/78.5 |
| 3,555,001 | 1/1971 | Wallis et al. ...................... | 260/112 |
| 4,081,432 | 3/1978 | Delente et al. ................... | 260/112 B |
| 4,097,473 | 6/1978 | Lewis et al. ...................... | 260/122 |
| 4,157,431 | 6/1979 | Fields et al. ...................... | 526/15 |

OTHER PUBLICATIONS

Lawn et al., *Nucleic Acids Res.* 9 (22), 6103–6114 (1981).
McGraw-Hill's *Biotechnology Newswatch*, vol. 1, No. 8, p. 1, Dec. 21, 1981.
*Applied Genetics News*, May 1982, p. 8.

*Primary Examiner*—Howard E. Schain
*Attorney, Agent, or Firm*—Scott J. Meyer; James W. Williams, Jr.

[57] ABSTRACT

Plasma proteins are separated from cell culture systems such as, for example, fermentation broths of microbial cell cultures and expended media of mammalian cell cultures, by adsorption with water-insoluble, cross-linked polyelectrolyte copolymers.

19 Claims, No Drawings

SEPARATION OF PLASMA PROTEINS FROM CELL CULTURE SYSTEMS

BACKGROUND OF THE INVENTION

This invention relates to a method for the separation of blood plasma proteins from cell culture systems such as, for example, fermentation broths of microbial cell cultures and expended media of mammalian cell cultures.

The fractional separation of the various species of proteins which occur in human plasma or serum has been the concern of scientists in the medical and pharmaceutical fields for many years. A significant part of this interest involves investigations for isolating the plasma components responsible for the clotting of blood, that is the blood coagulation factors. Other blood protein components of great medical interest are the gamma globulins, which are the carriers of antibody activity, and albumin, which is the main regulator of the colloid-osmotic pressure of plasma.

The most important of these plasma protein species are today harvested on an industrial scale with the natural source material being human donor blood. The importance of the isolation of blood plasma protein species is readily illustrated by the need for a commercial supply of antihemophilic factor (AHF; Factor VIII). The criticality of Factor VIII in hemostasis and blood coagulation is well-known. Most patients with a congenital clotting disorder have a Factor VIII deficiency (hemophilia A patients) while a lesser number have Factor IX deficiency (hemophilia B patients) or other minor coagulation factor deficiencies. Patients suffering from such clotting deficiencies have in the past relied upon transfusions of whole blood plasma or, preferably, on administration of plasma concentrates which have been purified to contain higher levels of Factor VIII or Factor IX. Cryoprecipitates such as developed by Judith Pool, New Eng. J. Med. 274, 1443–47 (1965), or still more concentrated fractions such as Hemofil® AHF, produced by methods described in U.S. Pat. Nos. 3,415,804, 3,631,018, 4,089,944 and Re. 29,698, are typical examples of commercially available fractions having high levels of Factor VIII. These commercially produced fractions depend, however, on the availability of a scarce commodity, namely a limited supply of donor blood.

With recently developed techniques of genetic engineering and molecular biology applied to the traditional processes of industrial microbiology, it is now feasible to produce mammalian plasma proteins in microbial species. Thus, the principal architects of gene splicing have disclosed the applicability of their methodology to the production of various plasma proteins such as antihemophilia protein, gamma globulins, albumin, fibrinogen and prothrombin. See Cohen and Boyer, U.S. Pat. No. 4,237,224, col.9. While the actual early work in genetic engineering was limited to the production of relatively small proteins such as somatostatin and insulin, the basic principles of gene splicing for the production of foreign proteins in bacteria and yeasts have now been shown to be adaptable to the preparation of much larger proteins. Thus, relatively large proteins which have already been produced by recombinant microorganisms are for example, ovalbumin having a molecular weight of about 43,000, as described in Ger. Offen. Nos. 2,923,297 and 2,933,000 and in Fr. Demande 2,458,585 and 2,476,126, and human serum albumin which has a chain of 585 amino acids, as described by Lawn et al., *Nucleic Acids Res.* 9 (22), 6103–6114 (1981).

The need to develop a useful method for the separation of plasma proteins from cell culture systems has now been recognized by the present inventor. The separation of any specific desired protein from admixture with other proteins and cell constituents, metabolites, cell debris and the like substances which are present in fermentation broths and expended media entails major difficulties. In the past, the recovery and isolation of protein products from fermentation broths and expended media has involved a variety of procedures such as:

Extraction by liberation from cells or cellular constituents by mechanical, physical or chemical disruption of the cell wall or membrane, for example, by use of homogenizers or by use of aqueous and organic solvent extraction;

Precipitation by salting out with salts such as $(NH_4)_2SO_4$, or by use of organic solvents such as ethanol, methanol or isopropanol, or high molecular weight polymers such as polyethylene glycol and dextran, or with metal ions and complexes, or by use of differential temperature and pH conditions;

Adsorption with colloidal materials such as bentonite, calcium phosphate, barium sulfate, hydroxyapetite, activated carbon, silica or $Al(OH)_3$ gels;

Centrifugation, filtration with or without filteraids such as kieselguhr and other such diatomaceous earths, or ultrafiltration;

Chromatography with gel filtration and ion-exchange resins such as with Sephadex® (cross-linked dextran) gels, Sepharose® (agarose) gels, and DEAE-Sephadex or DEAE-cellulose ion exchange resins;

Electrophoresis;

Ultracentrifugation; and

Finishing operations such as desalting, concentration and drying.

A more recently developed method for recovery and isolation of proteins involves immunoaffinity chromatography. Monoclonal antibodies having an affinity for a particular protein can be attached to polysaccharide beads which are placed in a chromatographic column. When the crude protein solution is passed through the column, the desired protein molecules are adsorbed on the beads while the impurities or undesired materials pass through the column. The desired protein is then eluted from the beads by adjustment in pH with a suitable washing solution.

DESCRIPTION OF THE INVENTION

In accordance with the present invention, plasma proteins are separated from admixture in cell culture systems by adsorption with water-insoluble, cross-linked polyelectrolyte copolymers. These polyelectrolyte copolymers are copolymers of olefinically unsaturated monomers having from 2 to about 4 carbon atoms and $\alpha,\beta$-unsaturated polycarboxylic acids or anhydrides having from 4 to about 6 carbon atoms and containing pendant diloweralkylaminoloweralkylimide functional groups.

As used herein, loweralkyl is defined to mean alkyl having from about one to about four carbon atoms.

Illustrative examples of suitable olefinically unsaturated monomers are ethylene, propylene and isobutylene; illustrative examples of suitable $\alpha,\beta$-unsaturated polycarboxylic acids or anhydrides are maleic, citraconic, itaconic and aconitic acids or anhydrides. Of these monomeric components, ethylene and maleic anhydride are preferred for the copolymeric formation. The copolymer also will preferably contain substantially equimolar quantities of the two component monomers.

Cross-linking of the copolymers to provide water-insolubility can be carried out with conventional cross-linking agents such as, for example, divinylbenzene and ethylene diamine. The preferred cross-linking agents are loweralkyliminobis(loweralkylamines) in which loweralkyl is defined as above.

The polyelectrolyte copolymers used in the present invention are known compounds which can be made according to methods described in U.S. Pat. Nos. 3,554,985; 3,555,001; 4,081,432; 4,097,473; 4,118,554; and 4,157,431. For example, the preferred copolymers of ethylene and maleic anhydride (EMA) can be prepared by reacting ethylene and maleic anhydride in the presence of peroxide catalyst in a suitable organic solvent medium. The resulting base EMA copolymer can be reacted with a cross-linking agent such as loweralkyliminobis(loweralkylamine) which has two primary amine groups and leads to a cross-linked EMA copolymer. The EMA preferably is reacted with from about 3 mole % to about 7 mole % of the cross-linking agent. The desired pendant diloweralkylaminoloweralkylimide functional groups can then be incorporated into the cross-linked copolymer by reaction of diloweralkylaminoloweralkylamine with part or all of the remaining free anhydride groups of the EMA copolymer. From about 3 mole % to about 100 mole % of the diloweralkylaminoloweralkylamine is used for preparing the polyelectrolyte copolymer adsorbents employed in the present invention.

A preferred diloweralkylaminoloweralkylamine is dimethylaminopropylamine and a preferred cross-linking agent is methyliminobis(propylamine).

The polyelectrolyte copolymers also can be prepared by methods which employ the aggregation step disclosed in U.S. Pat. No. 4,118,554 and any remaining free carboxyl or anhydride sites can be blocked with alkoxyalkylamine as disclosed in U.S. Pat. No. 4,157,431. Said alkoxy and alkyl preferably have from one to four carbon atoms and a most preferred blocking agent is methoxypropylamine.

It will be appreciated that disclosure of the foregoing methods of production of the polyelectrolyte copolymer adsorbents are for illustrative purposes only and that the method of separating the plasma proteins from cell culture systems in accordance with the present invention is not limited to any particular method of their preparation.

Although the polyelectrolyte copolymers have been known to be useful for the fractionation of blood serum and plasma, they have not heretofore been known to have, or suggested to have, ability to separate plasma proteins from fermentation broths of microbial cell cultures, expended media of mammalian cell cultures, and other such complex cell culture systems in which the plasma protein is in admixture with diverse proteins, peptides, nucleic acids and the like cell culture components. As used herein, the term cell culture system is defined to mean material liberated from the cultured cells such as, for example, a lysate or extract of the cells, or elaborated or introduced into the fermentation broth, or expended media, or found in any portion thereof which may contain the desired plasma protein.

The process of the present invention is adaptable to separate from cell culture systems any of the proteins normally found in plasma. This is illustrated in detailed examples hereinafter by separation of a blood coagulation protein, namely human Factor VIII, from bacterial, yeast and liver cell culture systems and by separation of another plasma protein, namely human serum albumin, from bacterial and yeast cell culture systems. Other plasma proteins such as, for example, $\alpha_1$-antitrypsin $\alpha_2$-macroglobulin, fibronectin, ceruloplasmin, C-reactive protein, transferrin, fibrinogen, prothrombin, plasma thromboplastin component and the gamma globulins can similarly be separated from cell culture systems by the method of this invention. The source of these plasma proteins in the cell culture systems can be from exogenous incorporation in the culture medium, for example, by introduction of plasma protein growth factors, whole blood serum such as horse, beef or sheep sera, or fetal bovine serum, as nutrients and the like, or can arise from specific production of the plasma protein by culture of genetically engineered cells.

In the case of the genetically engineered microorganisms, the initial genetic engineering can employ the typical four recombinant DNA elements as follows:
(1) methodology for breaking and joining DNA molecules derived from different sources,
(2) a suitable gene carrier that can replicate both itself and a foreign DNA fragment linked to it,
(3) a means for introducing the composite DNA molecule into a functional bacterial or yeast cell, and
(4) a method of selecting from a large population of cells a clone of recipient cells that has acquired the recombinant DNA molecule.

To illustrate, a bacterial plasmid, for example pSC101, can be used as a cloning vehicle to introduce a foreign or exogenous gene into the host bacteria. An illustrative host bacteria can be, for example, *Escherichia coli* K-12$\chi$1776, which is available from the American Type Culture Collection, Rockville, Maryland under accession number ATCC 31244. The plasmid can be cleaved with a restriction endonuclease or other DNA cleaving enzyme, for example EcoR I, to form a linear DNA fragment having an intact replicon and cohesive terminii. A second DNA fragment having the desired exogenous or foreign gene and a given phenotypical property and complementary ligatable terminii can be obtained from a foreign cell or chemically synthesized. This second DNA fragment is spliced with the first DNA fragment with a DNA ligase or other DNA ligating agent, for example $T_4$ DNA Ligase, to form a completely closed and recircularized plasmid. The insertion of the second DNA fragment into the EcoR I site of the illustrative plasmid brings the expression of the genetic information under the control of the lac operon controlling elements of the plasmid. The resulting recombinant plasmid is then used for transformation of the bacterial cell and allowed to replicate by growing the bacteria in a suitable culture medium. The desired transformants are then isolated by phenotypical trait differentiation, for example, by resistance to particular growth-inhibiting materials such as antibiotics or by various morphological property differences.

The applicability of the foregoing general principles of genetic engineering for the expression of mammalian plasma proteins in microorganisms is illustrated in practice by the production of human serum albumin (HSA) with recombinant bacteria as described by Lawn et al., *Nucleic Acids Res.* 9 (22), 6103–6114 (1981). According to the described procedure, a recombinant plasmid pHSA1 was constructed by conventional means to contain the mature protein coding region of the HSA gene. Bacteria containing this recombinant plasmid vector synthesize HSA protein under the control of the E. coli trp promoter-operator, which is that region of the E. coli chromosome that codes for enzymes involved in the synthesis of tryptophan.

For the construction of the pHSA1 plasmid, cDNA clones spanning the entire sequence of the protein coding and 3' untranslated portions of the HSA mRNA were isolated. Initial cDNA clones were obtained by priming human liver RNA with suitable oligodeoxythymidylates, namely oligo(dT)$_{12-18}$ (Collaborative Research). These cDNA clones were then used to construct the recombinant plasmid from a vector fragment that contained plasmid pBR322 sequences and a 300 bp fragment of the E. coli trp promoter, operator and ribosome binding site of the trp leader peptide terminating in the artificially blunt ended Xba I cleavage site derived from the plasmid pLeIF A25. The latter plasmid directs the expression of human leukocyte interferon A (IFN$\alpha$2) and is described by Goeddel et al., Nature 287, 411-416 (1980). The E. coli trp promoter-operator region is described also in Ger. Offen. 3,020,528, Japan Kokai Tokkyo Koho 80 61,798, Eur. Pat. Appl'n. 36,776, and by Russel and Bennet, Gene 17(1), 9-18 (1982). Plasmid pBR322 is a well characterized commercially available plasmid having a molecular weight of $2.6 \times 10^6$. It contains more than ten unique restriction sites, which includes a single Pst I restriction site within the ampicillin resistant (Ap) gene and single sites for the restriction endonucleases EcoR I, Hind III, BamH I, and Sal I, all located within or near the tetracycline resistant (Tc) gene. The significance of these single restriction sites is illustrated by the single site recognized by the restriction endonuclease Pst I, which cuts between the fifth and sixth bases of the sequence 5'CTGCA↓G3'. As there is only one Pst I site in pBR322, the cleavage results in a linear plasmid having short single stranded 3' ends. This plasmid is further described by Bolivar et al., Gene 2, 95 (1977) and its restriction endonuclease map has been published by Sutcliff, Nucleic Acids Res. 5, 2721-2728 (1978). It can be obtained from E. coli RR1, NRRL B-12014, a culture of which is on deposit in the permanent collection of the Northern Regional Research Laboratory, U.S. Department of Agriculture, Peoria, Ill. USA.

Several overlapping oligonucleotide recombinant fragments, designated as F-47, F-61 and B-44, were selected from the cDNA clones according to the aforesaid investigators to construct appropriate DNA strands for insertion into the above pBR322 modified vector fragment. Complementary cohesive terminii of the fragment blocks facilitated a three part assembly of the entire message sequence of the desired structural gene. The completed recombinant plasmid pHSA1 thus contained not only the Tc and Ap genes in the pBR322 portion of the plasmid and the E. coli trp promoter-operator region but also the HSA coding regions derived from the cDNA clones F-47, F-61 and B-44. Other selected restriction endonuclease sites in the recombinant plasmid pHSA1 were single EcoR I and Bgl II restriction sites and two Xba I and Pst I restriction sites.

The modified plasmid pHSA1 was then used to transform E. coli K-12 strain 294. When the E. coli containing the pHSA1 was grown in minimal media lacking tryptophan, the cells were reported to produce a protein which specifically reacts with HSA antibodies and comigrates with HSA in SDS polyacrylamide electrophoresis.

Other plasmid vectors can analogously be constructed for similar such expression of various plasma proteins in microbial cell culture systems by incorporating the appropriate genetic information in the recombinant plasmid. Thus, DNA coding for the polypeptide amino acid sequence of the desired protein can be prepared by selecting codons according to the genetic code. The engineered gene can then be inserted into an expression plasmid for replicating in a microbial host in a manner analogous to the above example for HSA.

Illustrative examples of microbial host vector systems applicable for genetically engineered production of mammalian proteins other than the E. coli K-12 host vector system which is described above for production of HSA are as follows:

Other Escherichia strains and other Enterobacteriaceae such as Salmonella;

Bacillus species such as B. subtilis, B. megaterium B. cereus, B. pumilus, B. amyloliquefaciens, B. licheniformis, and B. globigii;

Streptomyces species such as S. coelicolor, S. fradiae, S. parvulus, S. lividans, S. griseus, S. albus, and S. phaeochromogenes;

Staphyloccus species such as S. aureus; and

Yeasts such as Saccharomyces cerevisiae, Saccharomyces carlsbergensis, and Schizosaccharomyces pombe.

It is now apparent that virtually any piece of DNA can be ligated to ribosomal or any other genes that should integrate into the chromosome of the host. Axel and his associates have demonstrated that exogenous DNA can be taken up and expressed in cultured mammalian cells. Science 209, 1414-1422 (1980). Such techniques are useful for isolating genes that are not expressed in E. coli or other microbial hosts but which have distinct phenotypes in mammalian or other vertebrate cells. Transformed DNA is thus integrated into chromosomal DNA. The transforming DNA also can be introduced into cultured cells via the simian virus 40 (SV40) vector. The SV40 virus has thus been used as a vector for cloning many prokaryotic genes into mammalian cells. Mulligan and Berg, Science 209, 1422-1427 (1980). Actually, the first demonstration of recombinant DNA methodology was the introduction of the galactose operon of E. coli into SV40. Jackson et al., Proc. Nat. Acad. Sci. USA 69, 2904-2909 (1972). Other methods for isolating cloned DNA segments from defined regions of human chromosomes are described by Gusella et al, Proc. Natl. Acad. Sci. USA 77(5), 2829-2833 (1980).

It will be appreciated that the present invention is not limited to any particular host vector system for providing the plasma proteins by genetic engineering since the invention relates, instead, to separation of the plasma proteins from the cell culture system after growth of the cells in a suitable cell culture medium irrespective of the method whereby the plasma proteins are introduced into the culture system.

The chemical constituents of the cell culture medium will be such as to meet the elemental requirements for the cell mass and cell products and to supply appropriate energy for synthesis and maintenance. To illustrate, a typical elemental composition for a microbial cell can be as follows:

| Element | % of Cell Dry Weight |
| --- | --- |
| C | 50 |
| N | 7-12 |
| P | 1-3 |
| S | 0.5-1 |
| Mg | 0.5 |

An appropriate medium thus would be adapted to supply the stated elemental requirements for growth of the particular cell. Conventional media for small scale microbial cell culture are usually based on meat digest (tryptic digest, peptone, nutrient broth) which is the soluble product of the enzymatic hydrolysis of meat or fish. To provide vitamins and coenzymes (usually in mg/liter amounts) the media are frequently further enriched with meat extract (meat infusion) or yeast extract. Mineral salts such as NaCl, $K_2HPO_4$ and $MgSO_4$, and various amino acids may also be added as needed. In blood agar media, the blood will provide further nutrients. Sera may also be used in which the albumin component serves as a protective, nonnutrient growth factor. Carbon compounds such as glucose, lactose and maltose can provide the cell's needs for elemental carbon as well as produce the necessary energy.

To further illustrate, a typical minimal media for *E.coli* can be as follows:

| Substance | Gm/Liter |
| --- | --- |
| $K_2HPO_4$ | 7.0 |
| $KH_2PO_4$ | 3.0 |
| $Na_3$ citrate.$3H_2O$ | 0.5 |
| $MgSO_2.7H_2O$ | 0.1 |
| $FeSO_4$ | 0.01 |
| $(NH_4)_2SO_4$ | 1.0 |
| Glucose | 2.0 |

On a larger scale fermentation, suitable fermentation media can be prepared from carbohydrate materials such as whey, degraded corn starch, corn sugar, molasses, Cerelose ®, wheat bran and other sources of available carbon, and from nitrogenous materials such as Brewers' yeast, soya protein, casein, urea, ammonium salts, nitrates and other sources of available nitrogen. The sources of these fermentation media ingredients can be crude materials or more highly purified substances. N-Z-Amine ® protein hydrolysate, corn steep liquor and distillers' solubles are commercially available complex materials that can provide useful nutrient components for the microbial cell culture system. N-Z-Amine is an enzymatic digest of casein, which is a by-product of the dairy industry. Corn steep liquor is a by-product of the manufacture of corn starch and contains a complex of materials, including a variety of protein hydrolytic products, B-complex vitamins, amines, and other organic and inorganic materials. Distillers' solubles is a by-product from alcoholic beverage manufacture.

Trace nutrients that may be required by the microorganism are usually present with the major fermentation media ingredients such that separate addition of trace nutrients is not generally required. For example, trace amounts of inorganic salts such as metal chlorides, sulfates, phosphates and nitrates are generally present in the fermentation media in association with the major carbonaceous and nitrogenous ingredients.

Similarly, suitable culture media for the growth of mammalian and other vertebrate cells will contain assimilable sources of nitrogen, carbon and inorganic salts. These can be any of the well-known tissue culture media such as, for example, Basal Medium Eagle's (BME), Eagle's Minimum Essential Medium (MEM), Dulbecco's Modified Eagle Media, Medium 199, and balanced salt solutions (BSS) such as those of Eagle and Hanks fortified with various nutrients. These are commercially available tissue culture media and are described in detail by H. J. Morton, In Vitro 6, 89–108 (1970). These conventional culture media contain known essential amino acids, mineral salts, vitamins and carbohydrates. They also are frequently fortified with mammalian sera such as fetal bovine serum.

In view of the dominant role of the liver in biosynthesis of plasma proteins, liver cells are the preferred mammalian cells for culturing and separating plasma protein components therefrom in accordance with one aspect of the present invention. Cultures of tumor cells are particularly useful in the invention in the case of plasma components responsible for the clotting of blood. Thus, it is known that clotting abnormalities are commonly observed in patients with tumors, and fibrin deposits have been reported to surround many primary and transplated tumors in man and animals. See, for example, Dvorak et al., Science 212, 923–924 (1981). It is also known that albumin can be obtained from cultured hepatoma cells.

The separation of plasma components from mammalian cell culture systems is illustrated in detail hereinafter by separation of human Factor VIII from cell culture systems of the human liver adenocarcinoma cell line SK-HEP-1. The established cell line SK-HEP-1 was derived from a liver adenocarcinoma by G. Trempe of Sloan-Kettering Institute for Cancer Research in 1971, and cultures of the cell line are available from that institute. Prior publications on the establishment and characterization of cell line SK-HEP-1 include the following:

Fogh and Trempe, "New Human Tumor Cell Lines," in Human Tumor Cells In Vitro (Fogh, ed.), Plenum Publ. Corp., New York, 1975, pp. 115–54;

Fogh et al., J. Nat'l. Cancer Inst. 58, 209–14 (1977); and

Fogh et al., J. Nat'l. Cancer Inst. 59, 221–25 (1977).

In an illustrative example of the invention for the separation of Factor VIII proteins from cell culture systems, the polyelectrolyte preferably is a copolymer of ethylene and maleic anhydride cross-linked with from about 3 mole % to about 10 mole % of loweralkyliminobis(loweralkylamine), containing from about 3 mole % to about 7 mole % of pendant diloweralkylaminoloweralkylimide functional groups, and further characterized in that substantially all the remaining free carboxyl or anhydride sites are blocked with alkoxyalkylamine. Preferably, the copolymer is cross-linked with methyliminobispropylamine and the pendant functional groups are dimethylaminopropylimide. The concentration of the polyelectrolyte used in the separation process of this illustrative example will depend, in part, on the amount of Factor VIII in the cell culture system being treated but, in general, excellent results have been obtained when the polyelectrolyte has been used in a concentration of from about 1% to about 10% by weight and preferably from about 5% to about 6% by weight. The pH of the cell culture system preferably is adjusted to a level of from about 5.5 to about 6.5 during the Factor VIII adsorption step.

Separation of the adsorbed Factor VIII from the supernatant can be made by filtration, centrifugation and the like separation procedures. Elution of the Factor VIII protein can be had by washing the adsorbent with from about one to about three molar NaCl, preferably from about 1.5 to about 1.8 molar NaCl, and with other such physiologically acceptable eluants.

In another illustrative example of the invention for the separation of albumin from cell culture systems, the polyelectrolyte preferably is similar to the above-described material for Factor VIII except that the content of the pendant functional groups ranges from about 90 mole % to about 100 mole % and any remaining free carboxyl or anhydride sites can be blocked or remain unblocked. The concentration of the polyelectrolyte used in the separation process of this illustrative example will depend, in part, on the amount of albumin in the cell culture system being treated but, in general, excellent results have been obtained when the polyelectrolyte has been used in a concentration of from about 0.01 to about 20% by weight. The pH of the cell culture system preferably is adjusted to a range of from about 6.5 to about 7.5 during the albumin adsorption step. Separation of the adsorbed albumin from the supernatant and elution of the albumin from the adsorbent can be made in a manner similar to that described above for Factor VIII. During the elution step it is preferred to adjust the pH to a level of from about 3.5 to about 4.5 and to elute by employing about 0.01 to about 0.1 molar NaCl.

The following detailed examples will further illustrate the invention although it will be understood that the invention is not limited to these specific examples.

EXAMPLE 1

This example illustrates the separation of human plasma Factor VIII from bacterial and yeast cultures by adsorption with polyelectrolyte copolymers.

*Escherichia coli* bacteria and *Saccharomyces cerevisiae* yeast cells were cultured and processed under conditions as follows:

| A | |
|---|---|
| Culture medium for *E. coli*: | Luria Broth |
| | 17.5 g NaCl |
| | 17.5 g Yeast extract (Difco) |
| | 35.0 g Bacto-tryptone (Difco) |
| | 4.2 ml 2N NaOH |
| | 3500 ml Deionized distilled water |

The above materials were placed into solution by stirring and the solution was then autoclaved 30 minutes.
E. coli strain: K12.
Cultured: 48 hours at 37° C. in above medium.
Starting concentration: From 5 ml agar slant suspended in 3500 ml above medium.
Final concentrate: $5 \times 10^9$ cells/ml.
Cells were spun down at 3500 rpm for 10 minutes in a refrigerated Beckman J2-21 centrifuge.
Cell-free supernatant recovered: 3000 ml.
Cells recovered: 14.44 g.
Cell disruption: 8 g cells were disrupted in a French Press 4× at 12,000 psi per run.

B

Culture medium for yeast: YEPD

Solution (1): 25 g Yeast extract (Difco), 70 g Bacto-peptone (Difco), 3150 ml Deionized distilled water.
Solution (2): 70 g Dextrose, 350 ml Deionized distilled water.
Solution (3): 3.5 g $(NH_4)_2SO_4$, 17.5 ml deionized distilled water.

Solutions (1) and (2) were autoclaved separately. Solutions (1) and (2) while still warm after autoclaving but at reduced temperature were then combined in the following proportions with Solution (3):

| | |
|---|---|
| 6 × | { 450 ml solution (1) |
| | 50 ml solution (2) |
| | 2.5 ml solution (3) |

Yeast strain: M25.
Cultured: 48 hours at 30° C. in above medium with shaking.
Starting concentration: From 1.5 ml agar slant suspended in 3500 ml of above medium.
Final concentration: $5 \times 10^9$ cells/ml.
Cells were spun down at 3500 rpm for 10 minutes in a refrigerated Beckman J2-21 centrifuge.
Cell-free supernatant recovered: 2500 ml.
Cell recovered: 28.0 g.
Cell disruption: 8 g cells were disrupted in a French Press 4× at 15,000 psi per run.

A commercially available, highly purified concentrate of human plasma Factor VIII (Hemofil ® AHF*, Travenol Laboratories Inc.) was reconstituted in 10 ml sterile water and incubated in the above cell-free supernates and in suspensions of the above disrupted cells in physiological saline in dilutions of 30–190 ml. Factor VIII was then separated from the respective suspensions by adsorption with the following water-insoluble cross-linked polyelectrolyte polymer resin (Resin A).
*Processed as Method Four according to U.S. Patents 3,415,804; 3,631,018; 4,089,944 and Re. 29,698.

Resin A was a copolymer of substantially equimolar amounts of ethylene and maleic anhydride, cross-linked with 5 mole % of methyliminobis(propylamine), and containing 5 mole % of pendant dimethylaminopropylimide groups. All the free carboxyl or anhydride groups were further blocked with methoxypropylamine. This polyelectrolyte copolymer was made substantially according to methods with reactants and molar proportions as described in Example 1 of U.S. Pat. No. 4,157,431.

Prior to use, Resin A was preconditioned as follows:
Twelve grams of Resin A were slurried in 200 ml 0.154 M NaCl containing 0.1% bovine serum albumin (BSA) as a stabilizer. (Human serum albumin also can be used instead of BSA). The pH was adjusted to 4.0 with 1 M citric acid and the slurry was then filtered on a plastic Buchner funnel through Whatman #54 filter paper. The filtrate was discarded and the polyelectrolyte polymer cake was slurried in 200 ml 0.154 M NaCl containing 0.1% BSA. The pH was then adjusted to 5.8 with 1 N NaOH and stirred ten minutes at pH 5.8. The slurry was again filtered on a plastic Buchner funnel through Whatman #54 filter paper. The filtrate was discarded and the polyelectrolyte polymer cake was retained for further use below.

The separation process was carried out as follows:
Aprotinin protease inhibitor for Sigma Chemical Company (one ml, viz. 10–20 trypsin inhibitor units) was added as a stabilizer to 190 ml of the above-prepared *E. coli* culture supernate in a plastic beaker. After stirring for 3–5 minutes, 10 ml of reconstituted Hemofil AHF (264 units of Factor VIII) were added and the mixture was stirred and sampled for assay as sample (a) to establish an initial base line level. The mixture was then added to the above-retained polyelectrolyte polymer cake, the pH was adjusted to 5.8 with 1 M citric acid and stirred 20 minutes at pH 5.8. The slurry was filtered on a plastic Buchner funnel through Whatman #54 filter paper. Before the polyelectrolyte cake dried and cracked, the filtrate volume was measured and a sample (b) was removed. 200 ml of 0.002 M NaCl containing 0.1% BSA were then slowly poured over the polyelectrolyte cake. The filtrate was discarded and the cake was then dispersed in 200 ml of 0.3 M NaCl containing 0.1% BSA and stirred at pH 5.8 for five minutes. The slurry was filtered on a plastic Buchner funnel through Whatman #54 filter paper. Before the polyelectrolyte polymer cake dried and cracked, the filtrate volume was measured and a sample (c) was removed. 200 ml of 0.3 M NaCl containing 0.1% BSA was then used to wash the polyelectrolyte polymer cake and the filtrate was discarded. The polyelectrolyte cake was then dispersed in 200 ml 1.5 M NaCl containing 0.1 M lysine and 0.1% BSA stabilizers, the pH was adjusted to 6.0 with 1 M NaOH and the slurry was stirred 20 minutes at pH 6.0. The slurry was then filtered on a plastic Buchner funnel through Whatman #54 filter paper. The polyelectrolyte polymer cake was discarded and the filtrate was then refiltered on a plastic Buchner funnel through Whatman #1 filter paper. The volume of the resulting filtrate was then measured and a sample (d) was retained for assay.

The above polyelectrolyte adsorption procedures were repeated with the above yeast culture cell-free supernatant and with the above E. coli and yeast disrupted-cell suspensions.

Factor VIII assays were made on the above-retained samples by a conventional one-stage activated PTT (partial thromboplastin time) assay system* on an MLA Electra 750 Coagulation Timer (Medical Laboratory Automation, Inc.).

*Further background information on the one-stage PTT assay system can be had by reference to Quick, "Hemorrhagic Diseases," Lea & Febiger, Philadelphia, Pa., 1957; Langdell et al., *J. Lab Clin. Med.* 41. 637 (1953); and Hardisty et al., *Thromb. Diath. Haemorrh.* 7. 215 (1962).

This instrument employs optical sensing to indicate commencement of the clotting process. It measures the second derivative of the coagulation rate (i.e., the rate of change of the coagulation rate). The assay was made with the APTT (activated partial thromboplastin time) reagent kit Actin® and its procedure commercially supplied by Dade Diagnostics, Inc., which includes Factor VIII deficient plasma and an ellagic acid activator as described in U.S. Pat. No. 3,486,981. Coagulation times were determined for said dilutions of the test samples and results expressed as Factor VIII units recovered and percent of recovered Factor VIII activity based on the activity in the initial untreated sample (a). The results are set forth in the following Table I:

TABLE I

| Microbial Mixture | Factor VIII Activity (units/% of initial level) | | |
|---|---|---|---|
| | Unadsorbed Factor VIII Activity in Sample (b) | Factor VIII Activity in Wash Sample (c) | Recovered Factor VIII Activity in Sample (d) |
| E. coli cell-free supernate | 0.5/0.2% | 0.7/0.3% | 181/68.6% |
| E. coli disrupted cell suspension | 0.8/0.3% | 0.6/0.2% | 135/51.1% |
| Yeast cell-free supernate | 0.3/0.1% | 0.8/0.3% | 164/62.1% |
| Yeast disrupted cell suspension | 0.7/0.3% | 0.7/0.3% | 151/57.2% |

The results demonstrate the recovery of Factor VIII activity from the bacterial and yeast broths and disrupted cell suspensions in increased purity and in substantial yield.

EXAMPLE 2

This example illustrates the separation of human serum albumin from bacterial and yeast cultures by adsorption with polyelectrolyte copolymers.

*E. coli* and *S. cerevisiae* yeast cells were cultured and processed as in Example 1, above. Human serum albumin (Cohn Factor V; J.A.C.S. 68, 459, (1946) was incubated in the cell-free supernates and in dilutions of the liquid phase of the disrupted cells in physiological saline (30–190 ml dilutions). Albumin was then separated from the respective fractions by adsorption with the following water-insoluble, cross-linked polyelectrolyte polymer resin (Resin B):

Resin B was a copolymer of substantially equimolar amounts of ethylene and maleic anhydride, cross-linked with 5 mole % of methyliminobis(propylamine), and containing 90 mole % of pendant dimethylaminopropylimide groups. This polyelectrolyte copolymer was made substantially according to methods with reactants and molar proportions as described in Example 1 of U.S. Pat. Nos. 4,097,473 and 4,118,554 and Example 12 of U.S. Pat. No. 4,157,431.

In accordance with the present example, 2.4 ml of a 200 mg/ml solution of the albumin was thus admixed with 20 ml samples of each of the foregoing cell free supernates and disrupted cell dilutions. These samples were assayed for total protein content before and after the albumin spiking to establish a base line and an initial albumin level. Total protein content was determined with the Bio-Rad Protein Assay Kit which is commercially available from Bio-Rad Laboratories, Richmond, Calif. This kit provides a dye binding assay based on the method of Bradford, Anal. Biochem. 72, 248 (1976) and measures the differential color change of a dye in response to various concentrations of protein.

Twenty ml. of each of the albumin-spiked mixtures were then slurried with 200 mg of Resin B. The resin suspension was adjusted to pH 7.0, stirred for 30 minutes, filtered and the resin was then washed three times with about 50 ml. of deionized water each washing. The combined washings were assayed for total protein content as before. The resin cake for each sample was suspended in 20 ml. of 0.04 M NaCl, the pH was adjusted to 4.0 and the aqueous phase which contained eluted albumin was separated by filtration. The eluate samples were then assayed for total protein content as before. The final recovery of albumin was also determined by specific assay as described in "Albumin Standards and the Measurement of Serum Albumin with Bromcresol Green," Clin. Chem. Acta 31, 87 (1971). The foregoing assay results for total protein content and recovery of albumin are set forth in the following Table II:

TABLE II

| Assay Sample | Microbial Mixture | | | |
|---|---|---|---|---|
| | E. coli | | Yeast | |
| | Cell-free Supernate | Disrupted Cell Suspension | Cell-free Supernate | Disrupted Cell Suspension |
| TPC* (mg) Initial Base Line Samples | 0.43 | 67 | 0.65 | 71 |
| TPC (mg) Albumin Spiked Samples | 624 | 647 | 576 | 600 |
| TPC (mg) Wash Samples | 15 | 0.42 | 0 | 7 |
| TPC (mg) Eluate Samples | 431 | 456 | 337 | 433 |
| Recovery (% basis) Total Protein | 69.0 | 70.5 | 58.5 | 72.0 |
| Recovery (% basis Specific Albumin | 60.5 | 95.6 | 63.9 | 65.0 |

TPC = Total Protein Content

The above samples were also subjected to SDS-polyacrylamide gel electrophoresis. In the SDS electrophoresis, the samples were briefly heated with sodium dodecyl sulfate (SDS) and then subjected to 7% polyacrylamide gel electrophoresis at a constant 20-40 mA/gel and separated according to size by the molecular sieving effects of the gel. The migration rate correlates with the molecular weight. The gels were stained with Coomassie Blue R-250 and evaluated by density scanning techniques. The electrophoresis confirms the excellent separation of albumin from the complex admixture with other components of the microbial and yeast broths.

EXAMPLE 3

This example illustrates the separation of human plasma Factor VIII from human liver cell culture by adsorption with polyelectrolyte copolymers.

SK-HEP-1 liver cells were grown at 37° C. in Dulbecco's modified minimum essential medium (MEM) containing 4.5 mg/ml of glucose (KC Biologicals). The culture medium was supplemented with 5% by volume of bovine calf serum. The cells were first grown to confluency in attached culture in 75 cm² T-flasks (Falcon Plastics) and a portion of the cells were then transferred to and maintained in agitated liquid suspension culture in spinner flasks substantially in accordance with procedure described in U.S. Pat. No. 4,059,485.

Cells and cell-free supernates were recovered from the cell culture systems of the T-flasks and the spinner flasks. The cells were separated from the supernates by centrifugation and lysed by freeze-thawing 4 times.

A commercially available, highly purified concentrate of human plasma Factor VIII (AHF,* Cutter Laboratories, Inc.) was incubated in samples of the cell-free supernates and suspensions of the lysed cells in physiologically normal saline (0.9%, NaCl). Prior to such incubation, the dry Factor VIII was reconstituted in sterile water to provide 240 units per 10 ml of solution. A similar run of lysed cells from the spinner culture was made without the exogenous addition of Factor VIII (Run Z). The five runs of this Example are further designated as follows:

Run V—Lysed cells from T-flask culture;
Run W—Cell-free supernate from T-flask culture;
Run X—Lysed cells from spinner culture;
Run Y—Cell-free supernate from spinner culture; and
Run Z—Lysed cells from spinner culture.

*Purified from the cold insoluble fraction of pooled fresh frozen plasma by modification and refinements of methods described by Hershgold et al., J. Lab. Clin. Med. 67, 23-32 (1966).

The reconstituted Factor VIII was incubated in proportions as follows:

10 ml (240 Factor VIII units) were admixed with a suspension of 100 ml of the lysed cells from Run V in 90 ml of normal saline and one ml Aprotinin protease inhibitor;

10 ml (240 Factor VIII units) were added to 190 ml of the cell-free supernate of Run W and one ml Aprotinin protease inhibitor;

10 ml (240 Factor VIII units) were mixed with a suspension of 15 ml of the lysed cells from Run X in 175 ml of normal saline;

9.5 ml (228 Factor VIII units) were added to 191 ml of the cell-free supernatant from Run Y; and 15 ml of lysed cells from Run Z were added to 185 ml of normal saline without exogenous addition of Factor VIII.

The separation process was carried out as follows:

In the case of Runs X and Z, the samples were first mixed with 70.0 mg of Resin B (described in Example 2, above), the pH was adjusted to 8.0 and the slurry was stirred 20 minutes at this pH. The mixture was filtered on a Buchner Funnel through Whatman #54 filter paper. The resin was then scraped off the filter paper with distilled water into a beaker and stirred for 5 minutes. This mixture was filtered on a Buchner Funnel through Whatman #1 filter paper. The resin was discarded and the two filtrates were combined. The volume of the filtrate was recorded and a sample assayed as the Resin B unadsorbed fraction.

The samples from Runs V, W and Y (which were untreated with Resin B) and the above-treated samples of Runs X and Z (filtrates from Resin B treatment) were treated with preconditioned Resin A (described in Example 1, above) as follows:

The sample and resin were admixed, the pH was adjusted to 5.8 and the resulting slurry was stirred for 20 minutes at this pH. The slurry was filtered on a Buchner Funnel through Whatman #54 paper. Before the cake dried and cracked, the volume of the filtrate was noted, a sample was taken for assay as the Resin A unadsorbed fraction, and then 200 ml of 0.002 M NaCl solution with 0.1% BSA were poured over the cake and the total filtrate was discarded. The cake was dispensed in 200 ml of 0.3 M NaCl solution with 0.1% BSA and stirred 5 minutes at pH 5.8. The slurry was filtered on a Buchner Funnel through Whatman #54 filter paper. Before the cake dried and cracked, the volume of the filtrate was noted, a sample was taken for assay as the wash material, and then 200 ml of 0.3 M NaCl solution with 0.1% BSA was poured over the cake and the total filtrate was discarded. The resin cake was dispersed in 200 ml of an aqueous eluting solution of 1.5 M NaCl/0.1 M lysine/ and 0.01 M sodium citrate with 0.1% BSA and stirred 20 minutes at pH 6. The slurry was filtered on a Buchner Funnel through Whatman #54 filter paper. The resin cake was discarded and the resulting filtrate was re-filtered on a Buchner Funnel through Whatman #1 filter paper. The volume of the filtrate was noted and a sample was taken for assay as the final eluted Factor VIII fraction.

Factor VIII assays were made on the thus treated samples as in Example 1, above, and the results were expressed as Factor VIII units recovered. The results are set forth in the following Table III.

TABLE III

| Sample Assayed | Factor VIII Activity Units | | | | |
|---|---|---|---|---|---|
| | Run V | Run W | Run X | Run Y | Run Z |
| Lysed Cells | 93 | | 198 | | 198 |
| Lysed Cells + Factor VIII | 300 | | 602 | | |
| Cell-free Supernate | | 0 | | 3 | |
| Cell-free Supernate + Factor VIII | | 240 | | 228 | |
| Resin B Unadsorbed Material | | | 375 | | 104 |
| Resin A Unadsorbed Material | 6 | 1 | 3 | 2 | 3 |
| Wash Material | 3 | 2 | 3 | 5 | 2 |
| Final Eluted Factor VIII | 100 | 208 | 172 | 190 | 39 |

The results demonstrate recovery of Factor VIII activity from the liver cell cultures in all runs.

EXAMPLE 4

Substantially similar results as obtained in Examples 1-3, above, are obtained when propylene or isobutylene is substituted for an equivalent amount of ethylene, and/or when citraconic, itaconic or aconitic anhydride is substituted for an equivalent amount of maleic anhydride, and/or when diethylaminoethylamine is substituted for an equivalent amount of dimethylaminopropylamine in said Examples 1-3.

Various other examples will be apparent to the person skilled in the art after reading the present disclosure without departing from the spirit and scope of the invention and it is intended that all such other examples be included within the scope of the appended claims.

What is claimed is:

1. A process of separating a plasma protein component from its admixture in a cell culture system comprising adsorbing said plasma protein component therefrom by contact with a water-insoluble, cross-linked polyelectrolyte copolymer of olefinically unsaturated monomer having from 2 to about 4 carbon atoms and $\alpha,\beta$-unsaturated polycarboxylic acid or anhydride having from 4 to about 6 carbon atoms and containing pendant diloweralkylaminoloweralkylimide functional groups.

2. The process of claim 1 in which the cell culture system is a microbial cell culture system.

3. The process of claim 1 in which the cell culture system is a mammalian cell culture system.

4. The process of claim 2 in which the microbial cell culture system is a fermentation broth.

5. The process of claim 3 in which the mammalian cell culture system is an expended cell culture medium.

6. The process of claim 2 in which the microbial cell culture system is an isolate of disrupted microbial cells.

7. The process of claim 3 in which the mammalian cell culture system is an isolate of disrupted mammalian cells.

8. The process of claim 2 in which the microbial cells are bacteria cells.

9. The process of claim 8 in which the bacteria cells are *Escherichia coli* cells.

10. The process of claim 2 in which the microbial cells are yeast cells.

11. The process of claim 10 in which the yeast cells are *Saccharomyces cerevisiae* cells.

12. The process of claim 13 in which the mammalian cells are human liver cells.

13. The process of claim 12 in which the human liver cells are SK-HEP-1 cells.

14. The process of claim 1 in which the olefinically unsaturated monomer is ethylene and the $\alpha,\beta$-unsaturated polycarboxylic acid or anhydride is maleic acid or anhydride.

15. The process of claim 14 in which the diloweralkylaminoloweralkylimide is dimethylaminopropylimide.

16. The method of claim 1 in which the plasma protein is human plasma Factor VIII.

17. The method of claim 1 in which the plasma protein is human serum albumin.

18. The method of claim 16 in which the olefinically unsaturated monomer is ethylene, the $\alpha,\beta$-unsaturated polycarboxylic acid or anhydride is maleic acid or anhydride, the pendant diloweralkylaminoloweralkylimide is dimethylaminopropylimide and in which the polyelectrolyte copolymer contains from about 3 mole % to about 7 mole % of said pendant dimethylaminopropylimide and all the remaining free carboxyl or anhydride sites are blocked with alkoxyalkylamine wherein said alkyl and alkoxy have from one to about four carbon atoms.

19. The method of claim 17 in which the olefinically unsaturated monomer is ethylene, the $\alpha,\beta$-unsaturated polycarboxylic acid or anhydride is maleic acid or anhydride, the pendant diloweralkylaminoloweralkylimide is dimethylaminopropylimide and in which the polyelectrolyte copolymer contains from about 90 mole % to about 100 mole % of said pendant dimethylaminopropylimide.

* * * * *

UNITED STATES PATENT AND TRADEMARK OFFICE
CERTIFICATE OF CORRECTION

PATENT NO. : 4,382,028
DATED : May 3, 1983
INVENTOR(S) : G. Edward Paget

It is certified that error appears in the above—identified patent and that said Letters Patent is hereby corrected as shown below:

Claim 12, col. 16, line 24 "13" should read --3--.

Signed and Sealed this

Fourth Day of October 1983

[SEAL]

Attest:

GERALD J. MOSSINGHOFF

Attesting Officer     Commissioner of Patents and Trademarks